United States Patent [19]

Sittner

[11] 4,038,984

[45] Aug. 2, 1977

[54] METHOD AND APPARATUS FOR HIGH FREQUENCY ELECTRIC SURGERY

[75] Inventor: Weldon Rex Sittner, Englewood, Colo.

[73] Assignee: Electro Medical Systems, Inc., Englewood, Colo.

[21] Appl. No.: 239,095

[22] Filed: Mar. 29, 1972

Related U.S. Application Data

[63] Continuation-in-part of Ser. No. 8,549, Feb. 4, 1970, Pat. No. 3,675,655.

[51] Int. Cl.² ............................................. A61N 3/04
[52] U.S. Cl. .......................... 128/303.14; 128/303.17
[58] Field of Search ............ 128/303.1, 303.14, 303.17

[56] References Cited

U.S. PATENT DOCUMENTS

| | | | |
|---|---|---|---|
| 2,993,178 | 7/1961 | Burger | 128/303.14 X |
| 3,058,470 | 10/1962 | Seeliger et al. | 128/303.14 |
| 3,478,744 | 11/1969 | Leiter | 128/303.14 |
| 3,675,655 | 7/1972 | Sittner | 128/303.14 |
| 3,699,967 | 10/1972 | Anderson | 128/303.14 |
| 3,707,149 | 12/1972 | Hao | 128/303.14 |

*Primary Examiner*—Channing L. Pace
*Attorney, Agent, or Firm*—Klaas and Law

[57] ABSTRACT

A method and apparatus for electric surgery includes generating oscillations of high frequency electric energy of substantially constant amplitude, controlling the duration of and spacing in time between each series of oscillations generated and applying the generated energy through an electrode for the purpose of making surgical incisions and coagulating blood at the point of incision. A common generator serves as a source of the electric energy for different surgical procedures, the duration and spacing between each series of oscillations being closely controlled according to their intended application and in such a way as to minimize power requirements and the possible hazards of use either to the doctor or to the patient.

9 Claims, 7 Drawing Figures

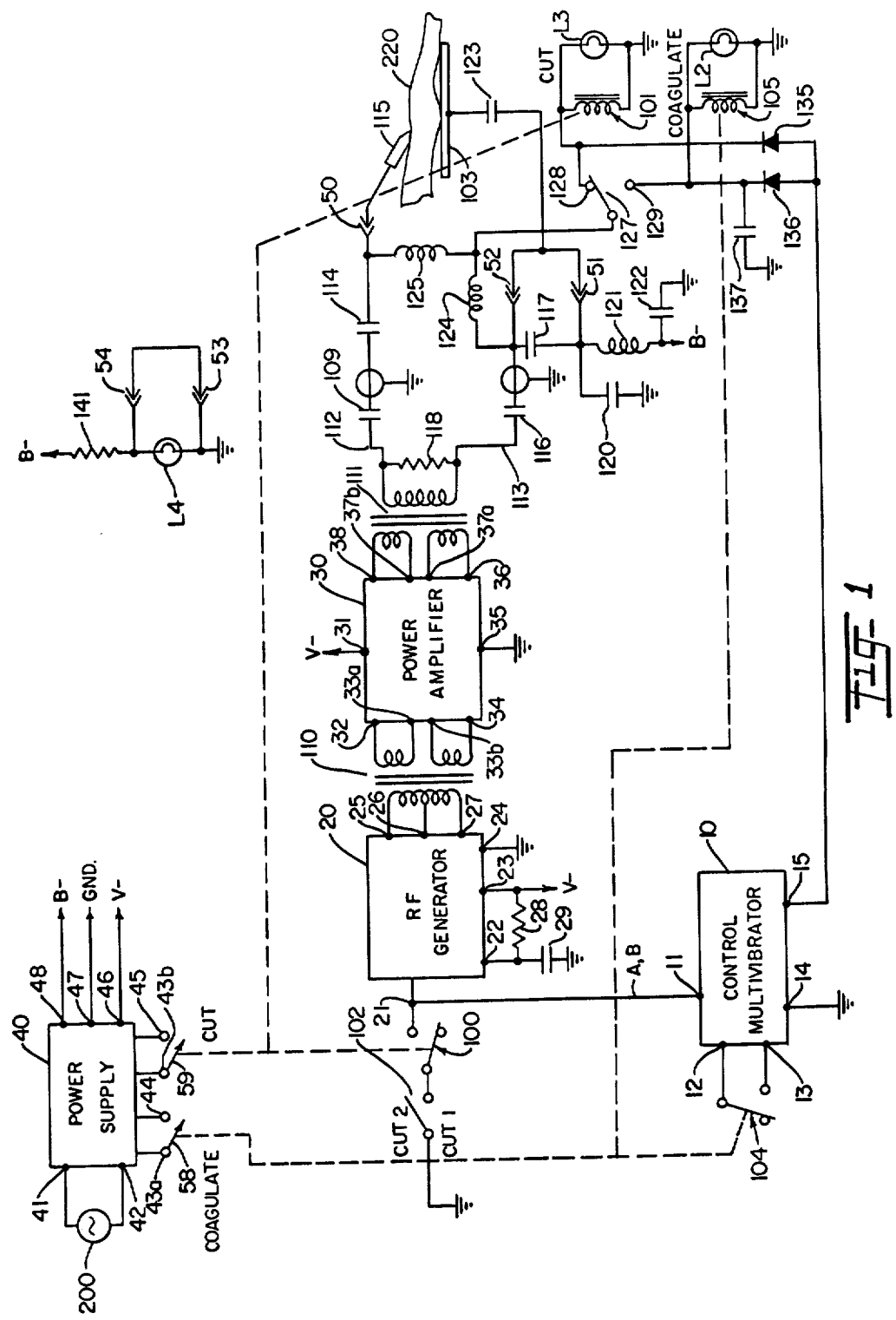

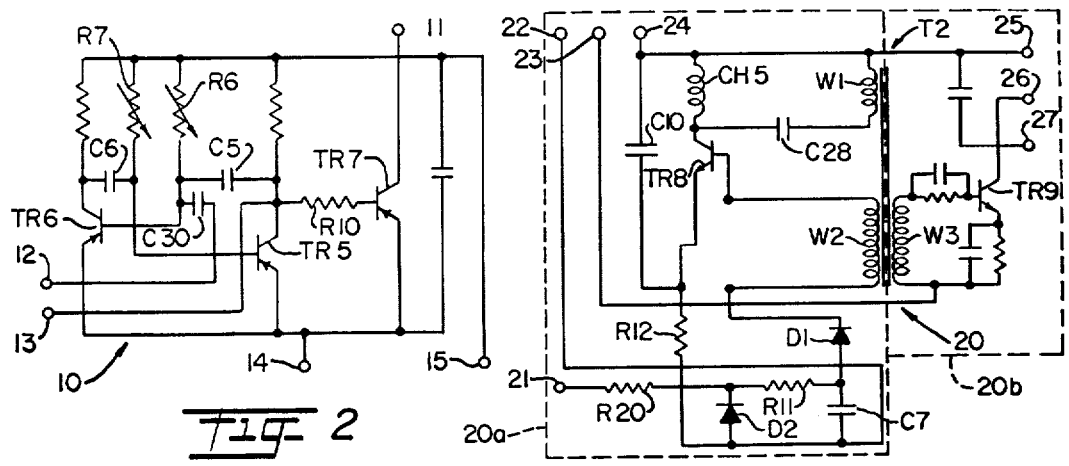

METHOD AND APPARATUS FOR HIGH FREQUENCY ELECTRIC SURGERY

This application is a continuation in part of application Ser. No. 8,549, filed Feb. 4, 1970 now U.S. Pat. No. 3,675,655.

This invention relates to medical electronic methods and apparatus, and more particularly to a method and apparatus for conducting electric surgery in a safe and highly efficient manner.

Heretofore, devices have been designed which have employed radio-frequency (RF) electric energy for performing surgery on the human body. Typically, such devices included a cutting mode of operation wherein a continuous waveform of RF energy produced by a vacuum tube generator was used to cut by means of the heat generated in the body tissue and a coagulation mode wherein a damped RF energy waveform provided by a separate spark-gap generator was used to coagulate the blood flowing from the cut tissues. A disadvantage with such prior art devices was that in order to perform the cut coagulation functions, two separate generators were required and which applied extremely high voltages to the active cutting electrode. Consequently, such devices and particularly the spark-gap generator unduly destroyed the tissue and further constituted significant hazards in their use, both for the patient and the operating physician.

Accordingly, it is an object of this invention to provide a novel method and apparatus for cutting tissues and coagulating and the blood at the area of the cut using the same RF generator and characterized by applying envelopes or packets of RF electric energy in an oscillatory waveform or substantially constant amplitude recurring at preselected spaced time intervals.

Another object of the present invention is to provide a novel apparatus for the high frequency electric surgery which obviates the aforementioned disadvantages of the prior art instruments by employing electric circuitry which enables the use of substantially lower RF voltages than heretofore possible and provides an essentially unmodified oscillatory waveform.

It is another object of the present invention to provide novel apparatus for high frequency electric surgery as set forth, which is capable of conducting both a cut mode of operation and a coagulation of mode of operation, either simultaneusly or independently of each other.

It is further an object of the present invention to provide a novel apparatus for high frequency electric surgery characterized by having an RF generator and control circuitry using solid state elements which is highly sensitive, reliable and efficient, and has close power regulation, and is closely adjustable and controllable in carrying out different selected surgical procedures and techniques in a safe dependable manner.

In accomplishing these and other objects, there has been provided in accordance with the present invention electric apparatus for performing high frequency electric surgery which includes an RF generator, and a control multivibrator, asymmetrical in operation, to control the RF generator to provide a combined cut and coagulation mode, and a coagulation mode of operation. Switching means are provided whereby the RF generator may be continuously operated or alternately controlled by the control multivibrator. The RF generator is connected to amplifying means for amplifying the RF power or energy generated by the RF generator and applying it to an active electrode for use in cutting or coagulating living body tissue. A return means in the form of a patient ground plate is positioned against the patient below the area of the body to be operated on for providing a return electrode path to the amplifying means. A power supply means supplies relatively low DC voltages to the apparatus circuitry. In this way there is provided by a single electronic oscillator circuit a series or envelopes of RF energy in an oscillatory waveform of substantially constant amplitude with the envelopes recurring at selected spaced time intervals for coagulation of blood or combined cutting and coagulation or the energy in a continuous waveform form for the usual cutting of body tissue.

DESCRIPTION OF THE DRAWINGS

FIG. 1 is partially a block diagram and partially a circuit diagram of an electric apparatus for high frequency electric surgery in accordance with the present invention;

FIG. 2 is a circuit diagram of the control multivibrator of FIG. 1;

FIG. 3 is a circuit diagram of the RF generator of FIG. 1;

FIG. 4 is a circuit diagram of the power amplifier of FIG. 1;

FIG. 5 is a circuit diagram of the power supply of FIG. 1;

FIG. 6 is a plan view of the patient ground plate of FIG. 1, and in part a circuit diagram of the connection of the patient ground plate into the circuitry of the apparatus of FIG. 1.

Referring to FIG. 1, the apparatus embodying the invention is shown to include a control multivibrator circuit 10 for controlling an RF generator circuit 20, the output of which is applied to a power amplifier circuit 30 for increasing the power output together with a power supply 40 which generates the DC voltage required by the aforementioned circuits. In FIG. 1, the RF generator 20 is shown to have a DC voltage supplied to generator terminals 22 and 23, generator terminal 24 being connected to ground. The DC voltage applied to terminals 22 and 23 is derived from the power supply 40 which generates DC voltages on its output terminals 46 and 48, terminal 47 being grounded. A V-voltage between terminal 47 and ground may be in the range of 0–180 volts, and is applied to generator terminal 23 and to terminal 22 through a resistor 28. An RF bypass capacitor 29 is connected between terminal 22 and ground.

Figure 7:
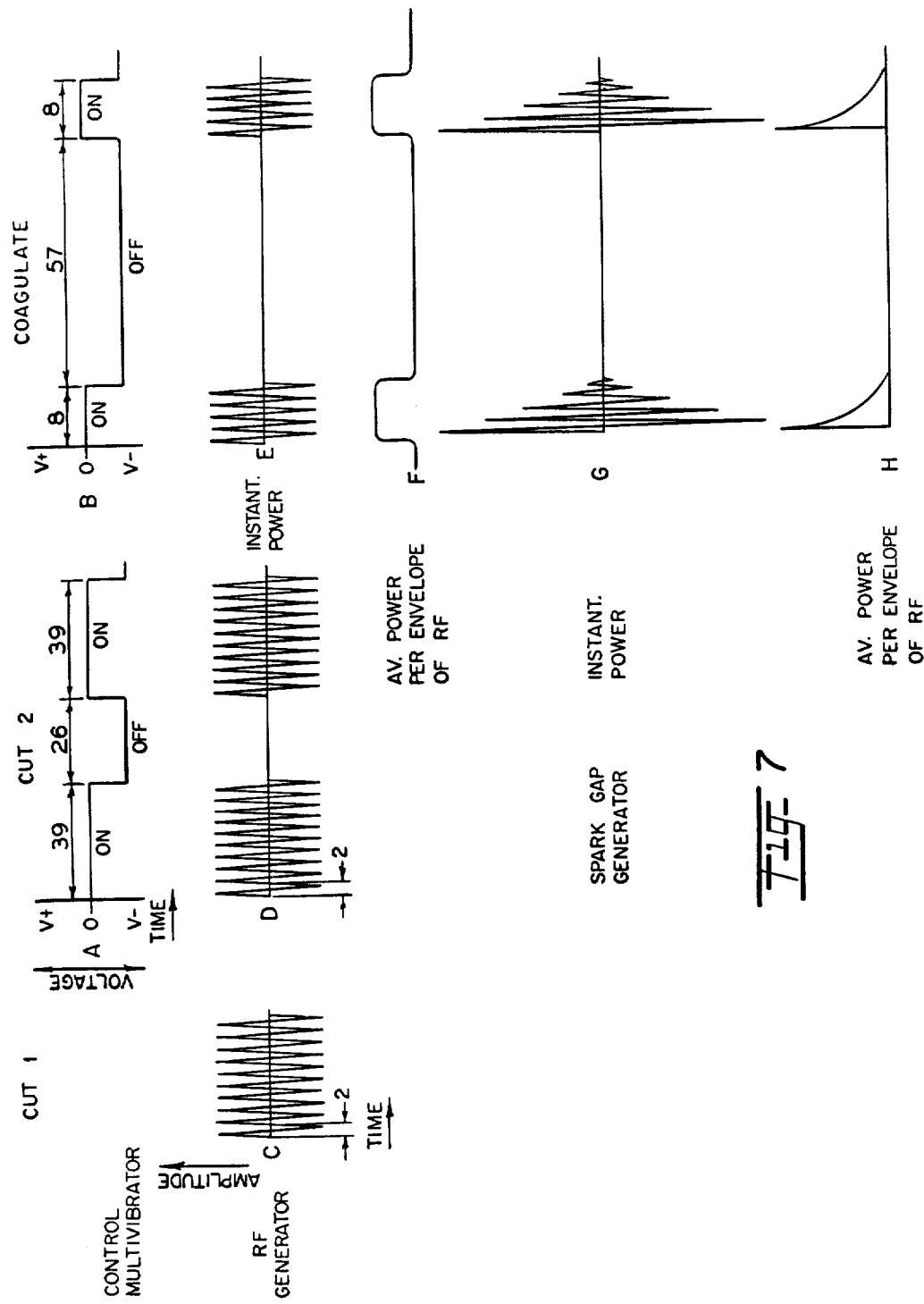
FIG. 7 is a showing of the output waveforms generated by the apparatus of FIG. 1 in its different modes of operation, together with a comparison of waveforms with typical spark-gap type generator.

The RF generator 20 has a control terminal 21 which is connected to the fixed contact of one set of relay contacts 100 of the relay 101, hereinafter referred to as the cut relay. A lamp L3 located on a control panel, is connected across relay 101 to indicate when the apparatus is in the cut mode. The other of the contacts 100 is a dummy contact while the movable contact arm is connected through an off-set switch 102 to ground. Switch 102, hereinafter referred to as the cut switch is a toggle type switch located on the control panel. In the open position shown, the cut mode switch 102 is set for cut 2 and in the closed position it is set for cut 1.

Connected also to the generator terminal 21 is the output terminal 11 of the control multivibrator 10. The control multivibrator 10 has DC voltage supplied to its terminals 14, 15, the terminal 14 being at ground, and B- voltage from the power supply 40 being supplied via the circuitry of a patient ground plate or indifferent electrode 103, to the terminal 15. The B- voltage generated by the power supply 40 may for example, be − 14 volts. The control multivibrator 10 has the movable contact arm of relay contacts 104 of the relay 105 connected to its terminal 12. Relay 105 serves as the coagulate relay and a lamp L2 located on the control panel is connected across coil 101 to indicate when the apparatus is in the coagulate mode. The multivibrator terminal 13 is connected to the other fixed contact of the relay contacts 104.

The RF generator 20 is transformer coupled by means of a step-up power transformer 110 to the power amplifier 30. The generator 20 has its output terminals 25–27 connected to the primary winding of transformer 110. The power amplifier 30 has its input terminals 32, 33a, 33b and 34 connected to the transformer 110. V- and ground are connected to the terminals 31 and 35, respectively, of the amplifier 30 to supply DC power thereto.

The output of the power amplifier 30 is coupled by a transformer 111 to output lines 112, 113. The primary winding of transformer 111 is connected to amplifier output terminals 36, 37a, 37b and 38. The output lines 112, 113 are connected across secondary winding of transformer 111. A resistor 118 is connected between the output lines 112, 113 across which is developed the output voltage of the transformer 111.

The output line 112 is a shielded line having its shield connected to ground and is connected through DC isolation capacitors 109 and 114 and through a terminal connect 50 to an active electrode 115. Terminal connect 50 permits the electrode 115 to be plugged into the control panel of the apparatus. The output line 113 is connected through a DC isolation capacitor 116 to terminal connects 51, 52 of the patients ground plate 103. A capacitor 117 is connected between the terminals 51,52 for the purpose of preventing a B- voltage from being supplied to the control multivibrator terminal 15 whenever the patient ground plate 103 is not electrically connected to the apparatus at terminals 51, 52. Connected to the side of capacitor 117 adjacent terminal 51 are a grounded capacitor 120 for DC isolation and an RF inductive choke 121 for isolating the power supply 40 from RF energy. A DC isolation capacitor 112 is also connected to the side of the choke 121 to which B voltage is supplied.

Terminals 51, 52 are mutually connected to a common point and from there are connected through a DC isolation capacitor 123 to the patient ground plate 103. Connected to the side of capacitor 117 common with terminal 52 is one terminal of an RF inductive choke 124. The other terminal of the choke 124 is connected through an RF inductive choke 125 to the ground plate 103. Connected to the side of the capacitor 117 common with terminal 52 is one terminal of an RF inductive choke 124. The other terminal of choke 124 is connected through an RF inductance choke 125 to the line 112 and also the movable contact with a switch 127. Switch 127 is preferably a treadle switch and foot operated by the physician and has fixed contacts 128, 129; and is used for switching the mode of operation of the apparatus between "cut" and coagulate.

The fixed contact 129 of switch 127 is connected through a diode 136 to the control multivibrator terminal 15. Similarly, the fixed contact 128 of the switch is connected through a diode 135 to the control multivibrator terminal 15. Thus, B- voltage may be supplied to terminal 15 through the electrical path defined by the choke 121, terminals 51, 52, choke 126, switch 127 and the appropriate diode 135 or 136. In this way, treadle switch 127 can not actuate the cut or coagulate relays unless the patient plate 103 is plugged into the apparatus. A capacitor 137 is also connected from switch contact 129 to ground.

The electrical means for connecting the patient ground plate 103 to the exemplary electrosurgical apparatus further includes terminals 53, 54 as shown in FIG. 6. The terminals 53, 54 are shorted together and serve to short out a lamp L4 whenever the plate 103 is connected to the above described apparatus. Terminals 51–54 are shown in FIG. 6 as mounted on a common plug indicated at 55. B- voltage is supplied to lamp L4 through a resistor 141. Lamp L4 is preferably located on the control panel and lit until the patient plate 103 is electrically plugged into the panel.

Referring to FIG. 2, the control multivibrator 10 is shown to include a conventional flip-circuit with transistor TR5, TR6 arranges to alternately conduct and cut-off in repetitive sequence. The bases of the transistors TR5, TR6 are connected to timing capacitors C6, C5 respectively. A third timing capacitor C30 is connected between one side of capacitor C5 and terminal 12 so that when terminals 12, 13 are connected by the actuation of relay 105, the total capacitance in one side of the flip-flop circuit is the sum of the capacitance of capacitors C5 and C30 instead of only capacitor C5. This shortens the period of conduction of transistor TR5 and thereby changes the duty cycle of the flip-flop circuit. Variable resistors R6, R7 connected to capacitors C5, C6, respectively may also be adjusted to vary the duration of the duty cycle on each side of the flip-flop circuit. Also included in circuit 10, as shown in FIG. 2, is a transistor TR7 having its base electrode connected through resistor R10 to the collector of TR5. The emitter-collector junction of transistor TR7 is connected between terminal 11 and grounded terminal 14. In this way, when transistor TR5 is conducting, a suitable voltage is applied to the base of transistor TR7 to cause it to conduct between its emitter and base electrodes and in effect connect terminal 11 to ground or zero potential via transistor TR7 which will enable the RF generator to run for a selected time interval when TR5 is conducting, and be off when TR5 is cut off during the "cut 2" and "coagulate" modes when terminal 21 is not grounded via contacts 100 and switch 102 as hereinafter more fully described.

Referring to FIG. 3, the RF generator circuit 20 is shown to include an RF oscillator circuit 20a transformer coupled by transformer T2 to a conventional driver amplifier circuit 20b. The driver amplifier circuit includes a transistor TR9 and functions to increase the power from the oscillator circuit 20a to the power amplifier circuit 30 and isolates the oscillator circuit therefrom.

The oscillator circuit 20a includes a transistor TR8 having its collector connected to a series resonant circuit of capacitor C 28 and winding W1 of transformer T2, with winding W1 having one end connected to grounded terminal 24. An Rf choke CH5 is connected between the collector and ground terminal 24 to provide an RF load for TR8. The emitter of transistor TR8 is connected to the V-voltage through bias resistors R12, R28. An RF bypass capacitor C10 connects between the emitter and ground terminal 24. The base of the transistor is connected to a regenerative feedback network including a feedback winding W2 of transformer T2, diode D2, which rectifies the RF energy induced in the winding W2 together with a charging capacitor C7 connected between the diode D1 and terminal 22. Resistors R11 and R20 are connected from a mutual connecting point with the diode D1 and capacitor C7 to control terminal 21 and a control diode D2 is connected between a mutual connecting point with resistors R11, R20 and to the V- voltage via resistor 28.

Oscillator circuit 20a will oscillate when terminal 21 is at ground or zero potential either via contacts 101 and switch 102 or via the conduction of transistor TR7. When terminal 21, connected to resistor R20, is at ground or zero potential, the feedback network has sufficient RF energy to enable the resonant circuit to sustain oscillations. More specifically, when terminal 21 is at ground diode D2 is back-biased and can not conduct. This establishes a timing circuit of C1 and R11 plus R20, the capacitor being charged by RF energy rectified by diode D1 which will produce sufficient energy in the feedback network to sustain oscillations. However, when terminal 21 is not grounded, diode D2 will conduct and, with only R11 and C7 forming the timing circuit for the feedback network, then there is insufficient RF energy available to sustain oscillations and the resonant circuit will continue to oscillate and induce RF power into winding W3 of the driver circuit. Under these conditions the potential at terminal 21 via diode D2 and resistor R20 is at the V-voltage and transistor TR7 will now conduct each time transistor TR5 conducts and cuts off each time transistor TR5 cuts off. In this way the flip-flop operates continuously when either relay 101 or 105 is actuated but during the cut 1 mode the control multivibrator is disabled since its collector is grounded via contacts 100 and switch 102.

Referring to FIG. 4, there is shown a conventional push-pull amplifier 30. The amplifier 30 has three serially connected transistor amplifier stages on each side consisting of transistors TR1, TR2 and TR3 on one side and transistors TR4, TR10 and TR11 on the other side. The amplifier 30 operates as a power amplifier to amplify the RF energy or power generated by RF generator 20. The power amplifier is driven relatively hard by the driver amplifier to achieve the desired performance.

Referring to FIG. 5, the power supply 40 includes input terminals 41, 42 with an AC electric power source signal generator 200 connected thereacross. The AC electric power source may, for example, be a conventional 115 volt 60 cycle power source to which the power supply 40 is connected. The power supply 40 also includes a conventional power control circuit 199 for varying the AC input by changing the phase and amplitude thereof and is available from General Electric Co. as G. E. TRIAC No. S100B3. This circuit includes a triac element 201 and a diac or double-based diode element 202 connected to the control electrode of the triac element 201. A pair of terminals 43a, 44 are provided for selectively connecting a variable resistor 203 into the power control circuit 199 to change its output for the coagulation mode, and similarly, a pair of terminals 43b, 45 electively connect a variable resistor 204 into the power control circuit 119 to change its output during the cut mode. Resistors 203, 204 are located on the control panel and are preset according to the power desired for either mode. The terminals 43a, 44 are shown as stationary contacts which are closed by a movable contact arm of the relay 105 which is selectively energized for the coagulate mode. Similarly, the terminals 43b, 45 shown as stationary contacts of relay 101 are selectively closed by a contact arm 59 movable in response to the energization of relay 101 for the cut mode as shown in FIG. 1. The power control circuit 199 is also adjustable by means of the variable resistor 205 to vary the output of the power supply.

Included in the power supply is a transformer 206 which couples the output of power source 200 to a diode bridge 207 to provide B- DC voltage across terminals 47, 48, and a transformer 208 couples the output of the power control circuit 199 to a diode bridge 209 to provide the V-DC voltage across terminals 46, 47. A power switch 211 located on the control panel connects the input power from supply 200 to the power control circuit 199 and a lamp L1 serves to indicate when the power is on to the power supply. A capacitor 212 is connected across terminals 47, 48 for filtering the 60 cycle power and a resistor 213 and capacitor 214 are connected across terminals 46, 47, the latter also being used to filter the 60 cycle power to assist in prevention of its being applied to the electrodes. In this way the waveform of the energy produced by the RF generator is not appreciably amplitude modulated by the 60 cycle power source 200. Vacuum tube type generators previously used for the cutting of tissue provide an amplitude modulated waveform which is modulated by the 60 cycle input power line to the extent of being completely modulated at 120 cycles. The effect of such amplitude modulation is to provide a series of envelopes of RF energy oscillations which decrease to substantially zero amplitude at one point in each repetition thereof.

In operation, the electrosurgical apparatus of the present invention, as shown in FIG. 1, is in situ with the active electrode 115 positioned to operate on a patient represented at 220. The indifferent electrode or patient ground plate 103 is placed in situ against the body of the patient, usually with the patient lying on plate 103. The power supply switch 211 is turned on and resistors 203 and 204 are set to the desired power levels. To make an incision or cut, cut switch 102 is closed for the cut 1 mode. The treadle switch 127 would be switched to the cut mode by the surgeon, thereby connecting the movable contact arm of switch 127 to its fixed contact 128. Thus, relay 101 is energized closing terminals 43b, 45 of power supply 40 and closing switch 100 to ground terminal 21 of RF generator 20 to turn said generator on to produce high frequency electric energy in an oscillatory waveform of substantially constant amplitude as represented at C in FIG. 7. Such RF electric energy is then amplified by power amplifier 30 and transformer-coupled to the electrodes 115, 103. The RF energy then flows from the active electrode 115 for selectively cutting the body tissue of the patient 220 and the energy returns to plate 103. The RF energy, after passing to plate 103, is then dissipated in RF chokes 121, 124 and 125.

After each cutting operation, or periodically in the cutting process, it is necessary to coagulate the blood flowing from the cut tissue. This is accomplished by operating the treadle switch 127 to switch the movable contact arm thereof to fixed contact 129. Relay 101 is deenergized while relay 105 is energized. Thus, contacts 100 open and terminal 21 is no longer grounded and contacts 104 close terminals 12, 13 of control multivibrator 10 to connect capacitor C30 in parallel with capacitor C5. Also, terminals 43a, 44 of power supply 40 are closed so that a higher level of power is generated by power supply 40 across output terminals 46, 47. In the coagulate mode, the potential at terminals 11, 21 alternately changes between two different electric potential levels with each level being of a selected duration which is established by the duty or timing cycle of the flip-flop circuit, and these potential or voltage levels in turn regulate the time on and time off for the oscillator circuit 20b. Thus, the voltage waveform at the output of control multivibrator 10 may be represented by a pulse-shaped waveform B as shown in FIG. 7. The voltage or potential level to turn the oscillator circuit on is zero or ground and this occurs as above described each time transistors TR5, TR7 conduct. However, when transistor TR5 cuts off, and the potential at terminals 11, 21 are a V-voltage supplied via resistors 28, diode D2 and R20 and this results in shutting the oscillator circuit off until TR7 again conducts as above described. Thus, the RF energy in the form of a series of envelopes of oscillations is generated by generator 20 as represented at E in FIG. 7 for each on-time for transitors TR5, TR7, this RF energy or electric power being amplified by power amplifier 30 and applied to electrodes 115, 103. Such RF electric energy may be characterized as envelopes or packets or a relatively short duration and recurring at regular intervals and operates through the active electrode 115 to coagulate the blood flowing from the severed blood vessels along the previously cut body tissue.

A third mode in which this apparatus may be operated is referred to as "cut 2" and in actuality is a mode in which the active electrode 115 both cuts and coagulates. In the cut 2 mode, treadle switch 127 may remain in the cut position to retain the energization of relay 101 and the cut power at terminals 46, 47; however, switch 102 is placed in the cut 2 position which opens the ground circuit to terminal 21. In this way, multivibrator 10 controls the enabling or on-time for the RF generator 20 and the disabling or off-time for said RF generator in the same manner as above described with reference to the coagulate mode. However, terminals 12, 13 of the multivibrator 10 are open and capacitor C30 is removed so that the on-time is longer and the off-time is shorter as represented by the waveform A in FIG. 7. The RF generator will then produce a series of envelopes of RF energy oscillations of a longer duration with shorter time intervals between each series, said energy being amplified and applied to electrodes 115, 103. This RF energy applied to active electrode 115 effects partially a cutting and partially a coagulating action on the body tissue of patient 220.

Reference is made to the waveforms of FIG. 7, to set forth the advantages of the present invention. The electrical resistance of the body tissues through which the RF current flows is essentially a resistance impedance and therefore, the waveforms of the RF current, RF voltage and instantaneous RF power are essentially the same as represented by waveform C, and may be characterized as being oscillatory and of substantially constant amplitude.

The actual frequency of this RF energy is determined by the "packet" widths used in the coagulate and cut 2 modes, but preferably is at least 0.3 MHz. In the "coagulate" mode, excellent results are obtained when the packet repetition period is from 20 to 100 microseconds, and a preferred period of about 50 microseconds. Waveform B shows a period of 65 microseconds with good results. Coupled with the repetition rate during one period is the actual duty cycle, i.e. the relation between the time the oscillations are present and the total time of one repetition period of the periodic waveform. Excellent results have been obtained for the above periods for the coagulate mode when the period is from 3 to 3 20 times longer then the packet width. Waveform B shows a duty cycle of ⅛, i.e. the period being 65 microseconds while the packet width is 8 microseconds. In the case of the example of waveform B, the RF energy had a frequency in the order of one half a MHz.

Accordingly, this produces a series of oscillations of RF energy of the same duration and recurring at regular intervals as represented by waveform E. The terms "envelope" or "Packet" as used herein are therefore intended to refer to a series of RF energy oscillations which occur during a particular duration or preselected time interval. Since the oscillations produced by generator 20 are of substantially constant amplitude, the positive and negative peaks define a rectangular area which may be considered as essentially rectangular shaped envelopes of RF energy. This is to be distinguished from RF energy produced by a spark-gap type generator which has damped oscillations and the instantaneous power of which decreases rapidly as represented by waveform G, in FIG. 7.

The significance of the difference between the outputs of the respective apparatuses is best understood by considering the average power waveforms for the two types of generators as represented by waveforms F and H. The generator 20 producing a series of envelopes of RF power E has an essentially flat average power characteristic over the duration of the envelope as represented at F, whereas that of the spark-gap type generator rapidly decreases to zero along a parabolic shaped curve of progressively decreasing slope as represented at H. Therefore, in order to provide equivalent average power over a similar duty cycle, the spark-gap generator requires considerably higher RF voltages and currents.

In the cut 2 mode, i.e., combined cutting and coagulating, the packet repetition period which produces excellent results, is from 20 to 100 microseconds, preferably 50 microseconds. The duty cycle for this cut 2 mode should range from ½ to 1/10, i.e., the repetition period is from twice to ten times longer then the packet width while the most desirable duty cycle is controllably variable between ⅛ and ⅛. Waveform A shows an example giving good results when the pulse repetition period was 65 microseconds and the duty cycle was 3/5.

Comparative tests show that the apparatus above described will operate at about 2400 volts peak-to-peak at the active electrode whereas in a spark-gap generator 6500 volts peak-to-peak is required. This difference in operating voltages is an important factor as concerns the safety of the patient, surgeon and operating personnel. Further, the AC power input to the vacuum tube type oscillator generator is about 1000 volts at 60 cycles, as compared to 117 volts for the cut 1 mode of the present apparatus; and the DC voltage of 1000 volts for the vacuum generator compares with a maximum of 180 volts for the present apparatus.

The average power of the instant apparatus to meet cutting power and peak coagulating power requirements may be less than 300 watts. In the coagulate mode, the average output power is from 10 to 200 watts and in the cut 2 mode, the average output power is from 10 to 300 watts. The output of generator 20 is in the range of 0-300 volts for the cut 1 mode and 0-400 volts for the cut 2 and coagulate modes, In turn, the output voltage at the active electrode is from about 0-1.1 KV for the cut 1 mode and about 0-1.5 KV for the cut 2 and coagulate modes. These ratings compare to a peak voltage for coagulation in the spark-gap generator of about 4.5 KV and peak power of about 6.5 KW.

In addition, the solid state elements employed herein provide a circuit of much improved reliability and efficiency, and closer power regulation over high frequency electrosurgical instruments heretofore available. The relatively low DC voltage of −14 volts used as the bias voltage for the transistors and for the treadle switch 127 which is preferably of the "explosion proof" type, is an additional safety factor. In the above described circuitry, the DC voltage and 60 cycle power line voltage are effectively isolated from the electrodes to minimize modulation of the main 60 cycle frequency which would otherwise affect the RF generator output and for patient safety.

I claim:

1. A method for high frequency electric surgery comprising the steps of:
    generating a continuous periodic waveform of high frequency electric energy wherein the period of the waveform is between fifty and sixty-five microseconds and within each period of the waveform there is at least one burst of substantially constant amplitude oscillations of high frequency electric energy with the duration of the burst being a predetermined fraction of the period of the waveform; and
    continuously applying the generated energy to a body site where a surgical change is desired in said body site.

2. A method for high frequency electric surgery comprising the steps of:
    generating a continuous periodic waveform of high frequency electric energy oscillating at a frequency of at least 0.3MHz wherein within each period of the waveform of the order of twenty to one hundred microseconds there is at least one burst of substantially constant amplitude oscillations of high frequency electric energy with the duration of the burst being a predetermined fraction of the period of the waveform; and
    continuously applying the generated energy to a body site where a surgical change is desired in said body site.

3. A method for high frequency electric surgery comprising the steps of:
    generating a continuous periodic waveform of high frequency electric energy wherein within each period of the waveform of the order of twenty to one hundred microseconds there is at least one burst of substantially constant amplitude oscillations of high frequency electric energy with the duration of the burst being a predetermined fraction of the period of the waveform and wherein the waveform is asymetrical and the duty cycle being less than one-half, the duty cycle being the ratio of the time oscillations are present during each period to the time of the period.

4. A method as in claim 3 wherein for coagulating the duty cycle is between one-third and one-twentieth.

5. A method as in claim 3 wherein for coagulating the duty cycle is one-fifteenth.

6. A method as in claim 3 wherein for combined cutting and coagulating the duty cycle is between less than one-half and one-tenth.

7. A method as in claim 3 wherein for combined cutting and coagulating the duty cycle is between less than one-half and one-eighth.

8. A method for high frequency electric surgery comprising the steps of:
    generating a continuous periodic waveform of high frequency electric energy wherein within each period of the waveform of the order of twenty to one hundred microseconds there is at least one burst of substantially constant amplitude oscillations of high frequency electric energy with the duration of the burst being a predetermined fraction of the period of the waveform, and wherein for combined cutting and coagulating the average power applied to said body site is no more than 300 watts.

9. A method for high frequency electric surgery comprising the steps of:
    generating a continuous periodic waveform of high frequency electric energy wherein within each period of the waveform of the order of twenty to one hundred microseconds there is at least one burst of substantially constant amplitude oscillations of high frequency electric energy with the duration of the burst being a predetermined fraction of the period of the waveform and wherein for coagulating the average power applied to said body site is no more than 200 watts.

* * * * *